United States Patent [19]

Kumagae et al.

[11] Patent Number: 5,376,617
[45] Date of Patent: Dec. 27, 1994

[54] CRYSTAL MODIFICATION OF 2-(3-METHYLANILION)-3-METHYL-6-DIETHYLAMINO-FLUORAN, PROCESS FOR THE PREPARATION THEREOF, AND RECORDING MATERIALS CONTAINING SAID CRYSTAL MODIFICATION

[75] Inventors: Yojiro Kumagae; Shigeo Fujita; Mansuke Matsumoto; Sayuri Wada; Shuuichi Hashimoto, all of Osaka, Japan

[73] Assignee: Yamamoto Chemicals, Inc., Osaka, Japan

[21] Appl. No.: 236,046

[22] Filed: May 2, 1994

Related U.S. Application Data

[62] Division of Ser. No. 989,566, Dec. 11, 1992, Pat. No. 5,338,866.

[30] Foreign Application Priority Data

Dec. 12, 1991 [JP] Japan .................................. 3-329119
Nov. 16, 1992 [JP] Japan .................................. 4-305537

[51] Int. Cl.$^5$ ............................................ B41M 5/20
[52] U.S. Cl. ..................................... 503/221; 549/226
[58] Field of Search ......................................... 503/221

[56] References Cited

U.S. PATENT DOCUMENTS 4,330,473 5/1982 Hatano et al. ...................... 549/226
4,502,068 2/1985 Taniguchi et al. .................. 503/216

FOREIGN PATENT DOCUMENTS

| 435149 | 12/1990 | European Pat. Off. . |
| 47-34422 | 11/1972 | Japan . |
| 49-17490 | 5/1974 | Japan . |
| 49-32767 | 9/1974 | Japan . |
| 178792 | 11/1982 | Japan . |
| 208092 | 12/1983 | Japan . |
| 59-68295 | 4/1984 | Japan . |
| 123556 | 7/1985 | Japan . |
| 116586 | 6/1986 | Japan . |
| 152486 | 7/1986 | Japan . |
| 283183 | 11/1989 | Japan . |
| 1357244 | 6/1974 | United Kingdom . |

Primary Examiner—C. Warren Ivy
Assistant Examiner—A. A. Owens
Attorney, Agent, or Firm—Browdy and Neimark

[57] ABSTRACT

The improved β-type crystal modification of 2-(3-methylanilino)-3-methyl-6-diethylaminofluoran has high solubility in inner-phase solvents. The compound is very useful as a color former for pressure-sensitive recording materials and thermal recording materials. Recording materials that use this compound as color former exhibit good performance in various characteristics such as whiteness of the background, its storage stability, color rendition, sensitivity for color formation and color fastness of image.

4 Claims, 4 Drawing Sheets

CRYSTAL MODIFICATION OF 2-(3-METHYLANILION)-3-METHYL-6-DIETHYLAMINO-FLUORAN, PROCESS FOR THE PREPARATION THEREOF, AND RECORDING MATERIALS CONTAINING SAID CRYSTAL MODIFICATION

This is a division of co-pending application Ser. No. 07/989,566 filed Dec. 11, 1992, now U.S. Pat. No. 5,338,866.

BACKGROUND OF THE INVENTION

This invention relates to a novel crystal modification of a fluoran compound, a process for its preparation and recording materials that use it.

More specifically, this invention relates to a novel crystal modification of a fluoran compound that is useful as an electron donating color former in recording materials such as a pressure-sensitive recording material and a thermal recording material. The invention also relates to a process for preparing said novel crystal modification, as well recording materials that contain said crystal modification and which exhibit superior characteristics.

Recording materials that make use of the color forming reaction between colorless or pale-colored electron donating color formers (hereunder referred to simply as "color formers") and organic or inorganic electron accepting color developers (hereunder referred to simply as "color developers") are well known and classified as pressure-sensitive recording materials, thermal recording materials, electrothermal recording materials, etc. Pressure-sensitive recording materials which are typically described in Japanese Patent Publication No. 20144/1987, etc. are used in such fields as vouchers and printers on computers. Thermal recording materials which are typically described in Japanese Patent Publication No. 14029/1970, etc. have a broad range of applications including recorders for instrumentation, facsimile, printers and automatic ticket vending machines.

Such recording materials are required to exhibit high performance in various respects including whiteness of background, storage stability of the background, color rendition, sensitivity for color formation, initial color density and storage stability of a color image, and it is essential to use color formers that specifically suit these purposes. Color formers for use in pressure-sensitive recording materials must satisfy an additional important characteristic requirement for high solubility in inner-phase solvent(s) (encapusulation oil(s)). Fluoran compounds are extensively used as color formers in various type of conventional recording materials.

While many compounds have already been known as fluoran compounds, one which has the same structural chemical formula as the fluoran compound according to the present invention [formula (1)] is disclosed in Japanese Patent Publication No. 17490/1974 and Japanese Patent Public Disclosure (Laid-Open) No. 34422/1972, which state that the compound has a melting point in the neighborhood of 158°–165° C. (this known fluoran compound is hereunder referred to as the "α-type crystal modification"). Pressure-sensitive recording materials using this α-type crystal modification exhibit low whiteness and lightfastness of the CB surface and the color image formed on those materials is also low in lightfastness. Thermal recording materials using this α-type crystal modification are low not only in background whiteness but also in the fastness of the color image formed on those materials.

Fluoran compounds of formulas (2) and (3) are also known to have chemical structures similar to that of the fluoran compound according to the present invention and they are described in Japanese Patent Publication Nos. 32767/1974 and 17490/1974:

The fluoran of formula (2), however, has the problem that it has too low a solubility in inner-phase solvent(s) to be effectively used as a color former in pressure-sensitive recording materials. Pressure-sensitive recording materials using this fluoran exhibit low whiteness and lightfastness of the CB surface and the color image formed on those materials is also low in lightfastness. Thermal recording materials using the fluoran (2) are low not only in the lightfastness of the background but also in the dynamic sensitivity for color formation and the storage stability of the color image formed on those materials. As a further problem, if the fluoran under consideration is used in common pressure-sensitive recording materials which use a zinc salt of a salicylic acid derivative as a color developer (which recording materials are hereunder referred to as "conventional pressure-sensitive recording materials") and in common thermal recording materials which use bisphenol A as a color developer (which recording materials are hereunder referred to as "conventional thermal recording materials"), the color rendered is purplish black and additional toning is necessary to attain a pure black color.

The fluoran of formula (3) has the problem that it has too low a solubility in inner-phase solvents to be effectively used as a color former in pressure-sensitive recording materials. Pressure-sensitive recording materials using this fluoran exhibit not only low whiteness of the CB surface but also insufficient lightfastness; in addition, the color image formed on those materials is low in lightfastness. Thermal recording materials using the fluoran (3) exhibit not only low whiteness and lightfastness of the background but also poor dynamic sensitivity for color formation; in addition, the storage stability of the color image formed on those materials is by no means sufficient. As a further problem, if the fluoran under consideration is used in conventional pressure-sensitive and thermal recording materials, the color rendered is greenish black and additional toning is necessary to attain a pure black color

SUMMARY OF THE INVENTION

An object, therefore, of the present invention is to provide a fluoran compound that is satisfactory in each of the characteristics to be possessed by color formers for use in various kinds of recording materials.

Another object of the present invention is to provide a process for producing said fluoran compound.

Still another object of the present invention is to provide recording materials that use said fluoran compound as a color former.

These objects of the present invention can be attained by a novel crystal modification of 2-(3-methylanilino)-3-methyl-6-diethylaminofluoran.

Thus, in its first aspect, the present invention relates to a β-type crystal modification of 2-(3-methylanilino)-3-methyl-6-diethylaminofluoran that is characterized by characteristic peaks at diffraction angles (2θ°±0.2°) of 7.6°, 12.2°, 14.9°, 15.9°, 17.6° and 22.8° on X-ray diffractiometry using Cu-Kα rays and which has a melting point in the range of 186–191° C.

In its second aspect, the present invention relates to recording materials that contain said β-type crystal modification as a color former.

In its third aspect, the present invention relates to a process for producing the β-type crystal modification by the steps of reacting a benzophenone compound of the formula (I):

with a diphenylamine compound of the formula (II):

(where R is a lower alkyl group) in the presence of a dehydrating/condensing agent, then treating the reaction product with an alkali, extracting the alkali-treated product with an organic solvent, and precipitating a fluoran from the extract, which process is characterized in that the total content of impurities in the organic solvent extract is no more than 10% of the extracted component.

The present invention also relates to a process for producing the β-type crystal modification by recrystallizing the α-type crystal modification with a solvent system comprising a mixture of at least one solvent selected from among methanol, ethanol, n-propanol, isopropanol, n-butanol and acetonitrile with at least one solvent selected from among benzene, toluene and xylene.

DETAILED DESCRIPTION OF THE PREFERRED EMBODIMENTS

The β-type crystal modification of the present invention is a novel compound that was first discovered by the present inventors. Heretofore, the compound represented by the chemical structural formula (1) has been available in the form of α-type crystal modifications that are produced by known processes described in patent publications. See, for example, Japanese Patent Publication No. 17490/1974, in which 2-(2-hydroxy-4-diethylaminobenzoyl)-benzoic acid is reacted with 2,3'-dimethyl-4-methoxydiphenylamine in the presence of conc. sulfuric acid at room temperature, the reaction product is then treated with an aqueous solution of caustic soda, and the resulting precipitate is extracted with toluene and crystallized to yield an α-type crystal modification having a melting point of 158°–160° C. Also see Japanese Patent Public Disclosure (Laid-Open) No. 34422/1972, in which 2-(2-hydroxy-4-diethylaminobenzoyl)benzoic acid is reacted with 2,3'-dimethyl-4-hydroxydiphenylamine in the presence of conc. sulfuric acid at 25° C. for 24 h, the reaction product is then neutralized with an aqueous solution of caustic soda, the resulting precipitate is heated under reflux in toluene in the presence of an aqueous solution of caustic soda and the toluene extract is concentrated to precipitate, yielding an α-type crystal modification having a melting point of 163°–165° C.

Figure 2:
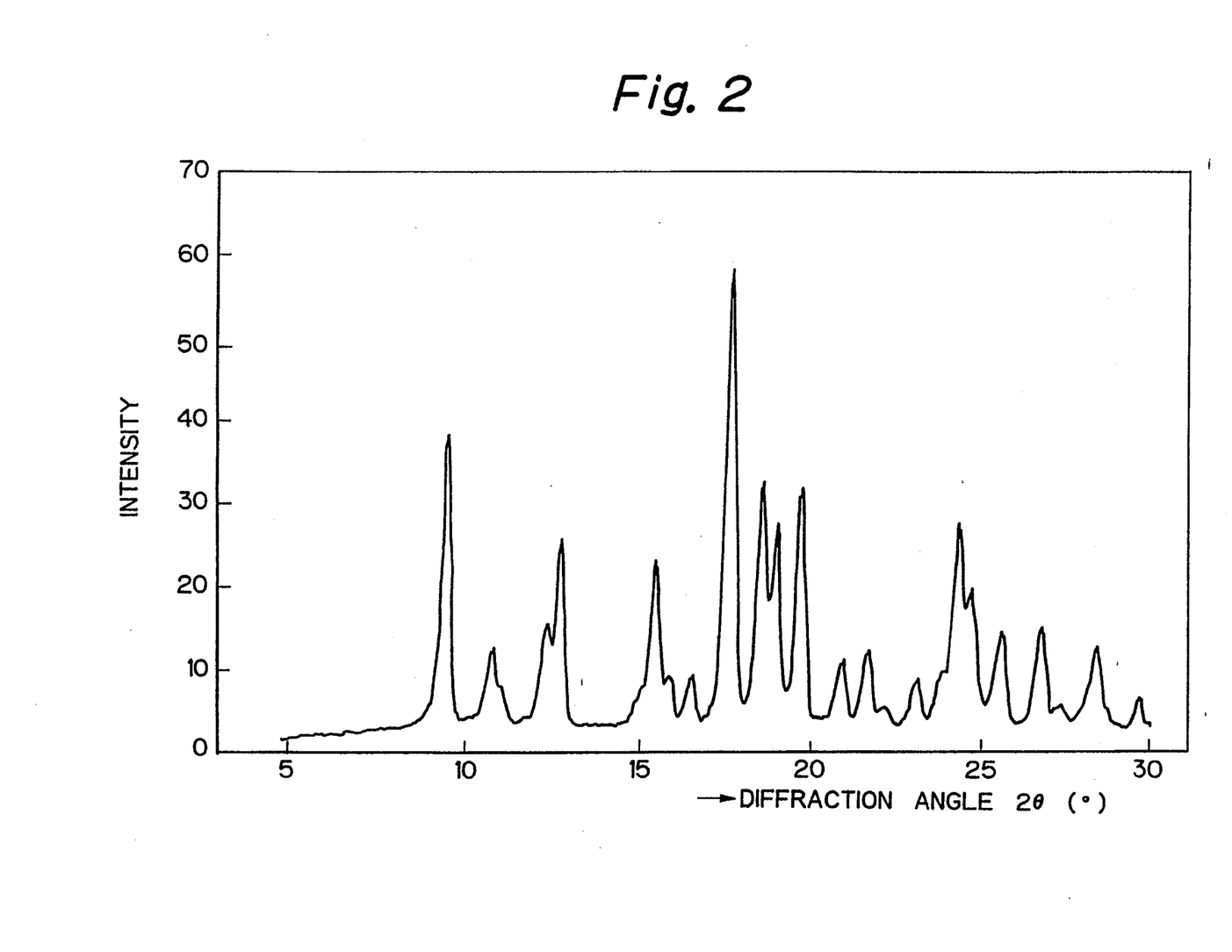
FIG. 2 is an X-ray diffraction diagram for the α-type crystal modification of 2-(3-methylanilino)-3-methyl-6-diethylaminofluoran as produced in Comparative Example 1.

These α-type crystal modifications are characterized by an X-ray diffraction diagram as shown in FIG. 2 which has characteristic peaks at diffraction angles (2θ°±0.2°) of 9.5°, 12.7°, 17.7°, 18.6°, 19.7° and 24.3° on X-ray diffractiometry using Cu-Kα rays.

As a result of intensive studies conducted in order to attain the aforementioned objects, the present inventors found that 2-(3-methylanilino)-3-methyl-6-diethylaminofluoran was also available in the form of a β-type crystal modification besides the known α-type crystal modification and that this β-type crystal modification had satisfactory characteristics for use as a color former in various kinds of recording materials.

By performing a reaction and treatments under the conditions to be specified hereinafter, a novel crystal modification (β-type crystal modification) of 2-(3-methyl-anilino)-3-methyl-6-diethylaminofluoran is produced. The present inventors found that when this β- type crystal modification was used as a color former in various kinds of recording materials, the latter exhibited far better characteristics than the known α-type crystal modification and fluoran compounds having similar structures.

The β-type crystal modification of the present invention can typically be produced by the following process:

A benzophenone compound represented by the formula (I):

is reacted with a diphenylamine compound represented by the formula (II):

(where R is a lower alkyl group) in the presence of a dehydrating/condensing agent and the reaction product is treated with an alkali.

For direct production of the β-type crystal modification in the present invention, the benzophenone compound represented by the formula (I) has desirably a purity of at least 96%, preferably at least 98% and, at the same time, the diphenylamine compound represented by the formula (II) has desirably a purity of at least 95%, preferably at least 97%. If the compounds of formulas (I) and (II) to be used have purities less than 98% and 95%, respectively, the impurities in the extract obtained by solvent extraction after the reaction and alkali treatment will increase to yield the α-type crystal modification; in this case, the α-type crystal modification has to be transformed to the β-type crystal modification by a suitable method such as recrystallization from a specific solvent.

As regards the diphenylamine compound represented by formula (II), the case where R is a methyl group is particularly preferred for the reason that smaller amounts of by-products will form when said compound is used in the reaction.

Exemplary dehydrating/condensing agents that can be used include conc. sulfuric acid, fuming sulfuric acid, poly(phosphoric acid), phosphorus pentoxide, etc. As already mentioned, it is important that the formation of impurities be minimized in order to achieve direct production of the β-type crystal modification of the present invention; hence, conc. sulfuric acid is particularly preferred.

The reaction temperature is in the range of 0°-100° C. and the reaction time is in the range of from several hours to several tens of hours. If conc. sulfuric acid is to be used as a dehydrating/condensing agent, the reaction temperature is preferably in the range of 0°-30° C., more preferably 5°-25° C., and the reaction time is preferably in the range of 5-48 h, more preferably 10-40 h, for the same reason as already mentioned above.

Exemplary alkalies that can be used include sodium hydroxide, potassium hydroxide, sodium carbonate, etc. For the same reason as already mentioned above, sodium hydroxide is particularly preferred. If sodium hydroxide is to be used as an alkali, it is preferably used as an aqueous solution. Treatment with alkalies is conducted at a temperature of 0°-100° C., preferably 50°-100° C.; generally speaking, the efficiency of this treatment increases with temperature.

Alkalies are preferably used in such amounts that the treating solution will have a pH of at least 9 or greater.

The alkali-treated reaction product is then extracted with an organic solvent. The organic solvent may already be present in the stage of alkali treatment.

Exemplary organic solvents that can be used include benzene, toluene, xylene, chlorobenzene, etc. and toluene is customarily used with preference. When the end product is precipitated from those organic solvents, methanol, ethanol, n-propanol and isopropanol may also be used.

For direct production of the β-type crystal modification in the present invention, the extract obtained by extracting the alkali-treated reaction product with an organic solvent must not contain more than 10% of impurities, preferably not more than 5% of impurities. Although it is not known exactly why the β-type crystal modification will not form unless the content of impurities in the solvent extract is 10% or less, the probable reason will be as follows.

The impurities the formation of which depends not only on the purities of the benzophenone compound of formula (I) and the diphenylamine compound of formula (II) but also on the reaction conditions such as the temperature and time of reaction in conc. sulfuric acid and which have not been removed even by alkali treatment will remain in the organic solvent extract.

If the total content of impurities in that organic solvent extract exceeds 10%, the precipitation of the end product from the organic solvent would be accompanied by the formation of α-type crystal modification on account of the effects of impurities, such as prolonged time of crystal precipitation.

If, in the production of 2-(3-methylanilino)-3-methyl-6-diethylaminofluoran, 2-(2-hydroxy-4-diethylaminobenzoyl)benzoic acid and 2,3'-dimethyl-4-hydroxydiphenylamine are used as starting materials as described in Japanese Patent Public Disclosure (Laid-Open) No. 34422/1972, the end product will be contaminated by particularly large amounts of by-products on account of the low reactivity of 2,3'-dimethyl-4-hydroxydiphenylamine.

From the viewpoint of yield and purity of the end product, it has conventionally been held that the diphenylamine represented by the formula (II) and analogous compounds are best produced by the process shown below that is described in Japanese Patent Publication No. 32767/1974 and which is already commercialized:

-continued (V)

(VI)

(where R has the same meaning as already defined; $R_3$ and $R_4$ each represents a hydrogen atom, a methyl group or an ethyl group; $R_5$ represents a hydrogen atom or a lower alkyl group; $R_7$ represents a lower alkyl group; X is a halogen atom: n is an integer of 1–5, provided that $R_3$ and $R_4$ are not a hydrogen atom at the same time).

However, this process has had the following disadvantage: in the case where the phenyl halide compound of formula (IV) used as one of the two starting materials is such that the alkyl group is in the m-position with respect to the halogen atom as exemplified by the case where it is m-bromotoluene, the diphenylamine of formula (II) which is produced using that phenyl halide compound tends to have a low purity.

-continued

(II)

(where R has the same meaning as already defined above).

However, even in this method, the diphenylamine represented by formula (II) which is derived from the compound of formula (VIII) tends to be of low purity.

These phenomena would provide one reason that explains why it has heretofore been impossible to produce the β-type crystal modification of 2-(3-methylanilino)-3-methyl-6-diethylaminofluoran.

Impurities that have been verified to occur as by-products in the production of α-type crystal modification of 2-(3-methylanilino)-3-methyl-6-diethylaminofluoran by known methods include: unreacted 2,3'-dimethyl-4-hydroxydiphenylamine and the sulfonated product thereof; unreacted 2,3'-dimethyl-4-methoxydiphenylamine and the sulfonated product thereof; 2,3'-dimethyl-4-methoxy-N-methyldiphenylamine; the sulfonated product of 2-(3-methylanilino)-3-methyl-6-diethylaminofluoran; and the compound (bislactone) represented by formula (X) shown below. Among these compounds, the one that is represented by formula (X) (bislactone) has been verified to occur most frequently:

The diphenylamine represented by formula (II) can also be produced in accordance with the following scheme:

(VII)  (VIII)

(IX)

The β-type crystal modification of the present invention can also be produced by recrystallizing a known α-type crystal modification with a solvent system comprising a mixture of at least one solvent selected from among methanol, ethanol, n-propanol, isopropanol, n-butanol and acetonitrile with at least one solvent selected from among benzene, toluene and xylene.

Exemplary xylenes that can be used include o-xylene, p-xylene, m-xylene and mixtures thereof.

At least one solvent selected from among methanol, ethanol, n-propanol, isopropanol, n-butanol and acetonitrile (of group A) and at least one solvent selected from among benzene, toluene and xylene (of group B) are preferably mixed at a ratio of from 1:1 (group A/group B) to 9:1 (group A/group B).

The amount of solvent system to be used varies with its type; if a mixture of methanol and toluene is to be used as the solvent system, it is preferably used in an amount 2–50 times the weight of the α-type crystal modification used.

Recrystallization may be performed in the usual manner; for instance, the α-type crystal modification is dissolved completely in a solvent system at a temperature in the range of from 40° C. to the reflux temperature, preferably at the reflux temperature, and, thereafter, the solution is cooled and the resulting precipitate is recovered by filtration.

The β-type crystal modification of the present invention has high solubility in inner-phase solvents for use in pressure-sensitive recording materials, such as commonly employed SAS-298 (Nippon Petrochemicals Co., Ltd.) and KMC-113 (Kureha Chemical Industry Co., Ltd.). Moreover, pressure-sensitive recording materials that use this compound as a color former exhibit high whiteness and lightfastness of the CB surface and can produce a pure black color, with the resulting color image exhibiting satisfactory storage stability.

When the β-type crystal modification is used as a color former in thermal recording materials, the recording materials exhibit high levels of background whiteness and storage stability; at the same time, they have high dynamic sensitivity for color formation and could produce a pure black color, with the resulting color image exhibiting satisfactory storage stability.

The β-type crystal modification of the present invention may be used in various kinds of recording materials. If necessary, it may be used either alone or in combination with other color formers.

Any color formers that are commonly used in recording materials of the types contemplated by the present invention may be used in combination with the β-type crystal modification described above. Particularly preferred color formers are those which are based on triphenylmethanephthalide, fluoran, fluorene, vinylogphthalide, etc. As specific examples, the following may be mentioned: 3,3-bis(p-dimethylaminophenyl)-6-dimethylaminophthalide; 2-anilino-3-methyl-6dimethylaminofluoran; 2-anilino-3-methyl-6-diethylaminofluoran; 2-anilino-3-methyl-6-dipropylaminofluoran; 2=anilino-3-methyl-6-dibutylaminofluoran; 2-anylino-3-methyl-6-dipentylaminofluoran; 2-anilino-3-methyl-6-(N-methyl-N-propylamino)fluoran; 2-anilino-3-methyl-6-(N-ethyl-N-isobutylamino)fluoran; 2-anilino-3-methyl-6-(N-ethyl-N-isopentylamino)fluoran; 2-anilino-3-methyl-6-(N-methyl-N-cyclohexylamino)fluoran; 2-anilino-3-methyl-6-(N-ethyl-N-tetrahydrofurfurylamino)fluoran; 3,6-bis(dimethylamino)fluorenespiro[9,3']-6'-dimethylaminophthalide; 3,3-bis{2,2-bis(p-dimethylaminophenyl)ethenyl}-4,5,6,7-tetrachlorophthalide; 3,3-bis{2,2-bis(1-ethyl-2-methylindol-3-yl)-ethenyl}-4,5,6,7-tetrachlorophthalide; etc. These color formers may be used either individually or as admixtures.

The β-type crystal modification of the present invention may be applied to pressure-sensitive recording materials by various known methods such as the one described in Japanese patent Publication No. 20144/1967, etc. A typical method is as follows: a solution of a color former in an inner-phase solvent is encapsulated with a polymeric compound being used as a membrane forming material; the dispersion of the capsules is coated on the back side of a base such as a wood-free paper, synthetic paper or plastic film to make an upper leaf; in a separate step, a color developer is coated on the obverse surface of another base to make a lower leaf; the upper and the lower leaf are superposed in such a way that their coated surfaces contact each other; when pressure is applied such as by writing or striking, the capsules in the area under pressure are disrupted, whereupon the color former in the capsules reacts with the color developer to form a recorded image on the surface of the lower leaf. More than one copy can be obtained by inserting between the upper and the lower leaf a plurality of intermediate leaves each comprising a base that has a color developer and capsules coated on the obverse and reverse surfaces, respectively.

The present invention is also applicable to other kinds of pressure-sensitive materials such as paper of a "self-contained" type which has both a color developer and capsules formed on the same side of a base, and a system in which either one of the color developer and the capsules is contained in a base whereas the other is coated on the base.

Examples of the color developer that can be used in pressure-sensitive materials include acid clay, zinc salts of salicylic acid derivatives, a zinc salt of p-octylphenol resin, p-phenylphenol resin, etc. Among these color developers, zinc salts of salicylic acid derivatives and a zinc salt of p-octylphenol resin are used with particular preference.

The β-type crystal modification of the present invention may be applied to thermal recording materials by various known methods such as the one described in Japanese Patent publication No. 14039/1970, etc. In a typical method, a color former, a color developer and a sensitizer are each dispersed in an aqueous solution of a water-soluble polymer such as poly(vinyl alcohol) by means of an attritor, a sand mill or the like until the particle size of each reagent is reduced to less than a few microns. The sensitizer may be added to either one or both of the color former and the color developer, so that they are dispersed simultaneously. If desired, the sensitizer may be dispersed as a preliminarily formed eutectic with the color former or the color developer. The thus prepared dispersions of the respective components are mixed together and any necessary ingredients such as a pigment, a binder, a wax, a metal soap, an antioxidant and a uv absorber are added so as to prepare a heat-sensitive coating dispersion. The coating dispersion is applied to a base such as wood-free paper, synthetic paper or plastic film and calendered to impart smoothness, whereby a desired thermal recording material is obtained. Depending on the necessity for providing improved color forming properties, the heat-sensitive coating dispersion may be applied onto a base having a precoat of heat-insulating layer of plastic pigment or silica, etc. Furthermore, if it is necessary to impart resistance to water and chemicals, a topcoat may be formed on the thermal recording layer using an aqueous solution of a water-soluble polymer, etc.

Various kinds of phenolic compounds may be used as color developers in thermal recording materials. Specific examples include: 2,2-bis(p-hydroxyphenyl)propane (commonly known as "bisphenol A"), 2,2-bis(p-hydroxyphenyl)-4methylpentane; 1,1-bis(p-hydroxyphenyl)cyclohexane; bis(p-hydroxyphenyl) sulfone (commonly known as "bisphenol S"); bisphenol S monoisopropyl ether; 3,3'-diallylbisphenol S; 1,5-bis(p-hydroxyphenylmercapto)-3-oxapentane; benzyl p-hydroxybenzoate; tetrabromobisphenol A and tetrabromobisphonol S. Among these phenolic compounds, bisphenol A may be used with particular preference.

Exemplary sensitizers include: p-benzylbiphenyl; m-terphenyl; 2-benzyloxynaphthalene; 1,4-dibenzyloxynaphthalene; dibenzyl oxalate; di-(p-methylbenzyl) oxalate; 1,2-diphenoxyethane; 1,2-di-m-toluoxyethane; 1,2-di-p-toluoxyethane; 1,4-diphenoxybutane; benzyl p-benzyloxybenzoate; phenyl 2-naphthoate; phenyl 1- hydroxy-2-naphthoate; dibenzyl terephthalate, etc. Among these sensitizers, p-benzylbiphenyl, m-terphenyl, 2-benzyloxynaphthalene, di-(p-methylbenzyl) oxalate and 1,2-di-m-toluoxyethane may be used with particular preference.

The pigments that can be used may be organic or inorganic. Specific examples of preferred pigments include calcium carbonate, barium sulfate, titanium oxide, aluminum hydroxide, amorphous silica, urea-formaldehyde resin powders and polyethylene resin powders.

The binders that can be used are water-soluble polymers and water-insoluble polymers. Specific examples of water-soluble polymers as preferred binders include: methyl cellulose, carboxymethyl cellulose, hydroxyethyl cellulose, starches, styrene-maleic anhydride copolymer hydrolyzate, ethylene-maleic anhydride copolymer hydrolyzate, isobutylene-maleic anhydride copolymer hydrolyzate, poly(vinyl alcohol), carboxymodified poly(vinyl alcohol) and polyacrylamide. Specific examples of water-insoluble polymers as preferred binders include: styrene-butadiene rubber latex, acrylonitrile-butadiene rubber latex, and vinyl acetate emulsions.

Specific examples of preferred waxes include paraffin wax, carboxy-modified paraffin wax and polyethylene wax.

Metal salts of higher aliphatic acids may be used as metal soaps and specific-examples of preferred metal soaps include zinc stearate, calcium stearate and aluminum stearate.

Hindered phenols may be used as antioxidants. Ultraviolet absorbers that can be used are those which are based on benzophenone and benzotriazole.

The following examples are provided for the purpose of further illustrating the present invention but are in no way to be taken as limiting.

EXAMPLE 1

Figure 1:
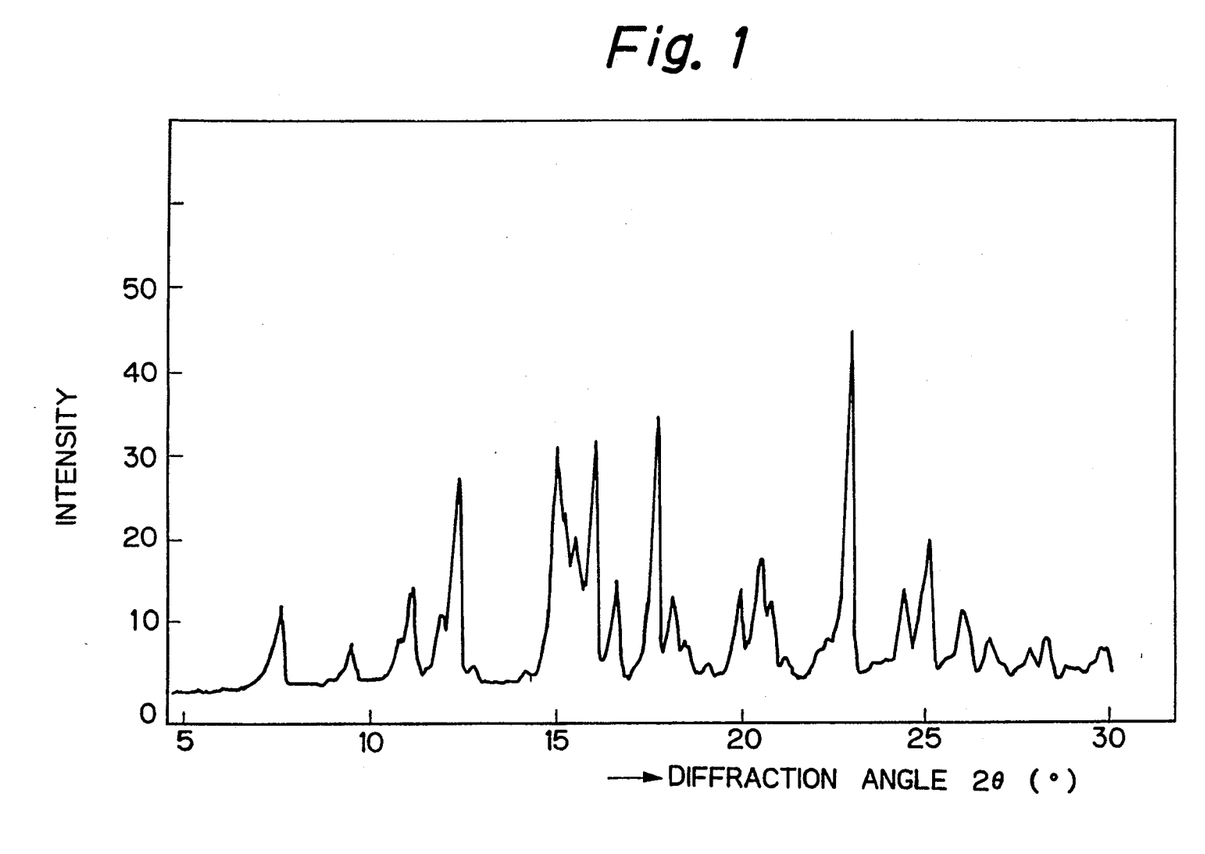
FIG. 1 is an X-ray diffraction diagram for the β-type crystal modification of 2-(3-methylanilino)-3-methyl-6-diethylaminofluoran as produced in Example 1.
Figure 3:
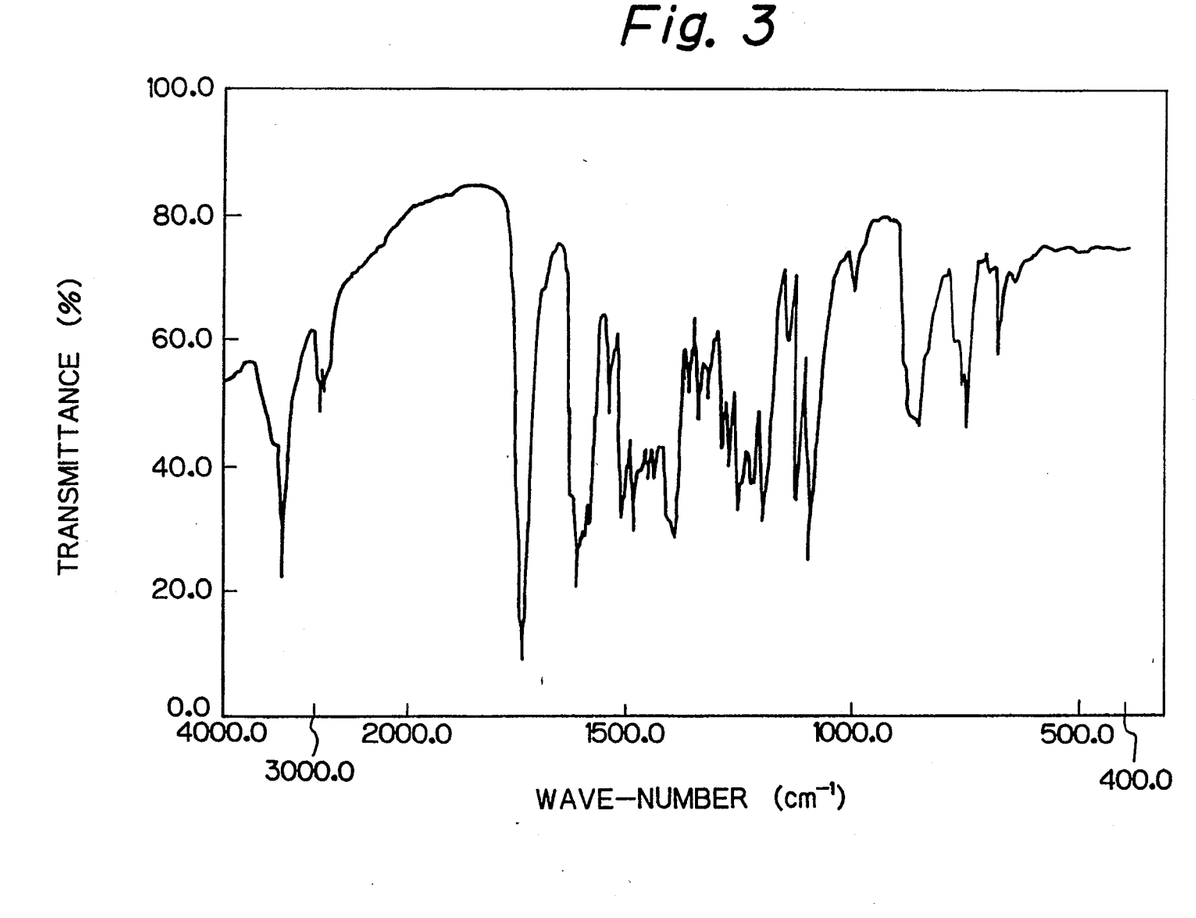
FIG. 3 is an infrared absorption spectrum of the β-type crystal modification of 2-(3-methylanilino)-3-methyl-6-diethylaminofluoran as produced in Example 1.

Production of the β-Type Crystal Modification of 2-(3-methylanilino)-3-methyl-6-diethylaminofluoran To 100 ml of 98% sulfuric acid, 31.3 g of 2-(2-hydroxy-4-diethylaminobenzoyl)benzoic acid having a purity of 98.1% was added in small portions at 25° C. or below to form a complete solution. Thereafter, 23.8 g of 2,3'-dimethyl-4-methoxydiphenylamine having a purity of 97.2% was added dropwise at 10°–20° C. The mixture was stirred at room temperature for 20 h and the reaction product was discharged into 1000 g of ice water. The resulting precipitate was recovered by filtration and refluxed under agitation for 1 h with 200 ml of toluene and 130 ml of an aqueous solution of 25% sodium hydroxide. Subsequently, the toluene layer was separated out and washed with warm water. When the toluene extract was subjected to compositional analysis by high-performance liquid chromatography, the total amount of impurities was found to be 2% of the extracted component. The toluene solution was concentrated under vacuum to 100 ml and cooled. The resulting precipitate was recovered by filtration and recrystallized from 80 ml of toluene. Isopropyl alcohol (500 ml) was added to the resulting crystal and the mixture was stirred under reflux for 1 h, followed by cooling. The resulting crystal was recovered by filtration and dried to produce a pale yellowish white crystal in an amount of 33.4 g (yield: 68.1%). The melting point of the crystal, as well as its elemental analysis, parent peak of mass analysis and characteristic absorption of IR absorption spectrum were as listed below. An X-ray diffraction diagram for the crystal is shown in FIG. 1 and its IR absorption spectrum in FIG. 3.

m.p. 188°–189° C.

| Elemental analysis for $C_{32}H_{30}N_2O_3$ | C | H | N |
|---|---|---|---|
| Cal'd: | 78.34% | 6.16% | 5.71% |
| Found: | 78.30% | 6.18% | 5.68% |

MS (m/e): 490 (M+)
IR: $\nu$ NH 3370 cm$^{-1}$

EXAMPLE 2

Production of the β-Type Crystal Modification of 2-(3-methylanilino)-3-methyl-6-diethylaminofluoran To 100 ml of 98% sulfuric acid, 31.3 g of 2-(2-hydroxy-4-diethylaminobenzoyl)benzoic acid having a purity of 98.5% was added in small portions at 25° C. or below to form a complete solution. Thereafter, 23.8 g of 2,3'-dimethyl-4-methoxydiphenylamine having a purity of 97.8% (as prepared in accordance with the method described in Japanese Patent Public Disclosure No. 193949/1985) was added dropwise at 10°–20° C. The mixture was stirred at 15°–20° C. for 20 h and the reaction product was discharged into 1000 g of ice water. The resulting precipitate was recovered by filtration and refluxed under agitation for 1 h with 200 ml of toluene and 130 ml of an aqueous solution of 25% sodium hydroxide. Subsequently, the toluene layer was separated out and washed with warm water. When the toluene extract was subjected to compositional analysis by high-performance liquid chromatography, the total amount of impurities was found to be 1.2% of the extracted component. The toluene solution was concentrated under vacuum and 300 ml of methanol was added to the residue, followed by standing at room temperature for 15 h. The resulting crystal was recovered by filtration and dried to produce a pale yellowish white crystal in an amount of 44.6 g (yield: 91%). The melting point and elemental analysis of the crystal were as listed below. An X-ray diffraction diagram for the crystal, as well as its parent peak of mass analysis and IR absorption spectrum were the same as those of the crystal obtained in Example 1.

m.p. 189°–190° C.

| Elemental analysis for $C_{32}H_{30}N_2O_3$ | C | H | N |
|---|---|---|---|
| Cal'd: | 78.34% | 6.16% | 5.71% |
| Found: | 78.35% | 6.17% | 5.73% |

Comparative Example 1

Figure 4:
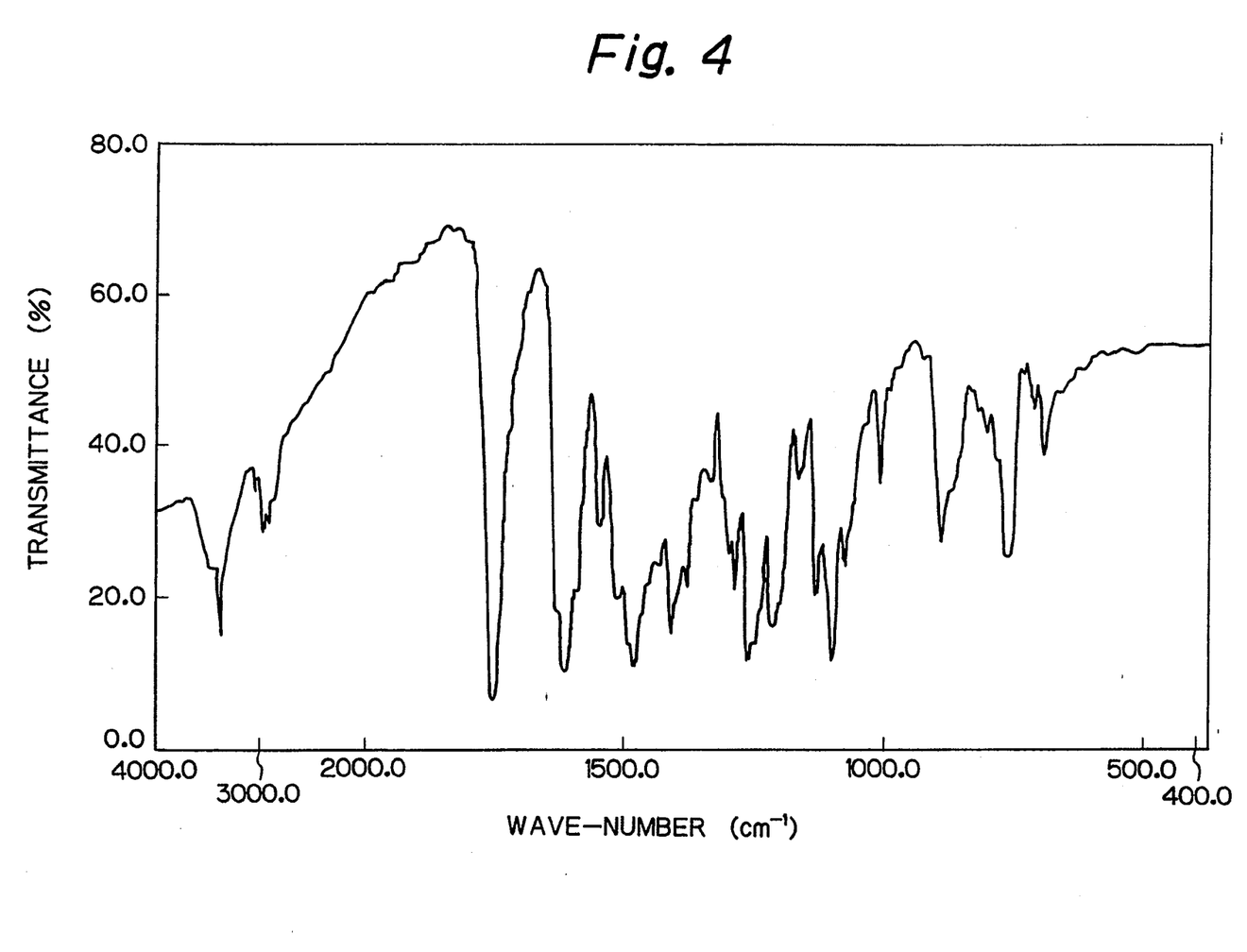
FIG. 4 is an infrared absorption spectrum of the α-type crystal modification of 2-(3-methylanilino)-3-methyl-6-diethylaminofluoran as produced in Comparative Example 1.

Production of the α-type Crystal Modification of 2-(3-methylanilino)-3-methyl-6-diethylaminofluoran To 100 ml of 98% sulfuric acid, 31.3 g of 2-(2-hydroxy-4-diethylaminobenzoyl)benzoic acid having a purity of 92% was added in small portions at 25° C. or below to form a complete solution. Thereafter, 23.8 g of 2,3'-dimethyl-4-methoxydiphenylamine having a purity of 90.5% was added dropwise at 10°–20° C. The mixture was stirred at 28°–30° C. for 20 h and the reaction product was discharged into 1000 g of ice water. The resulting precipitate was recovered by filtration and refluxed under agitation for 1 h together with 200 ml of toluene and 130 ml of an aqueous solution of 25% sodium hydroxide. Subsequently, the toluene layer was separated out and washed with warm water. When the toluene extract was subjected to compositional analysis by high-performance liquid chromatography, the total amount of impurities was found to be 13.5% of the extracted component. The toluene solution was concentrated under vacuum to 100 ml and cooled. Following the addition of methanol (500 ml), the mixture was left to stand at room temperature for 15 h. The resulting crystal was recovered by filtration and dried to produce a pale yellowish white crystal in an amount of 33.3 g (yield: 68%). The melting point of the crystal, as well as its elemental analysis, parent peak of mass analysis and characteristic absorption of IR absorption spectrum were as listed below. An X-ray diffraction diagram for the crystal is shown in FIG. 2 and its IR absorption spectrum in FIG. 4.

m.p. 158°–160 ° C.

| Elemental analysis for $C_{32}H_{30}N_2O_3$ | C | H | N |
|---|---|---|---|
| Cal'd: | 78.34% | 6.16% | 5.71% |
| Found: | 78.51% | 6.20% | 5.56% |

MS (m/e): 490 (M+)
IR: $\nu$ NH 3385 cm$^{-1}$

Comparative Example 2

Production of the α-Type Crystal Modification of 2-(3-methylanilino)-3-methyl-6-diethylaminofluoran To 100 ml of 98% sulfuric acid, 31.3 g of 2-(2-hydroxy-4-diethylaminobenzoyl)benzoic acid having a purity of 98.1% was added in small portions at 25° C. or below to form a complete solution. Thereafter, 23.8 g of 2,3'-dimethyl-4-methoxydiphenylamine having a purity of 97.2% was added dropwise at 10°–20° C. The mixture was stirred at 28°–30° C. for 70 h and the reaction product was discharged into 1000 g of ice water. The resulting precipitate was recovered by filtration and refluxed under agitation for 1 h together with 200 ml of toluene and 130 ml of an aqueous solution of 25% sodium hydroxide. Subsequently, the toluene layer was separated out and washed with warm water. When the toluene extract was subjected to compositional analysis by high-performance liquid chromatography, the total amount of impurities was found to be 12.6% of the extracted component. The toluene solution was concentrated under vacuum to 100 ml and cooled. Following the addition of methanol (500 ml), the mixture was left to stand at room temperature for 15 h. The resulting crystal was recovered by filtration and dried to produce a pale yellowish white crystal in an amount of 34.8 g (yield: 71%). The melting point and elemental analysis of the crystal were as listed below. An X-ray diffraction diagram for the crystal showed the same characteristic peaks as the crystal obtained in Comparative Example 1, and its parent peak of mass analysis and IR absorption spectrum were also the same as those exhibited by the crystal obtained in Comparative Example 1.

m.p. 160°–162° C.

| Elemental analysis for $C_{32}H_{30}N_2O_3$ | C | H | N |
|---|---|---|---|
| Cal'd: | 78.34% | 6.16% | 5.71% |
| Found: | 78.38% | 6.25% | 5.68% |

Comparative Example 3

Production of the α-Type Crystal Modification of 2-(3-methylanilino)-3-methyl-6-diethylaminofluoran To 110 g of 98% sulfuric acid, 15 g of 2-(2-hydroxy-4-diethylaminobenzoyl)benzoic acid having a purity of 98.1% was added in small portions at 25° C. or below to form a complete solution. Thereafter, 12.2 g of 2,3'-dimethyl-4-hydroxydiphenylamine having a purity of 96.3% was added dropwise at 10°–20° C. and the mixture was stirred at 25° C. for 24 h. The reaction product was diluted by being discharged into 250 g of ice water and thereafter neutralized with 500 ml of an aqueous solution of 20% sodium hydroxide. The precipitating crystal was recovered by filtration and refluxed under agitation for 1 h together with 500 ml of toluene and 100 ml of an aqueous solution of 2% sodium hydroxide. Insoluble matters were filtered off and the toluene layer was separated out, washed with three 100 ml portions of 2% HCl and further washed with water. When the toluene extract was subjected to compositional analysis by high-performance liquid chromatography, the total amount of impurities was found to be 14.8% of the extracted component. The toluene solution was concentrated under vacuum to 50 ml and cooled. The resulting precipitate was recovered by filtration, mixed with 300 ml of methanol and left to stand at room temperature for 15 h. The resulting crystal was recovered by filtration and dried to produce a pale yellowish white crystal in an amount of 14.5 g (yield: 61.7%). The melting point and elemental analysis of the crystal were as listed below. An X-ray diffraction diagram for the crystal showed the same characteristic peaks as the crystal obtained in Comparative Example 1, and its parent peak of mass analysis and IR absorption spectrum were also the same as those exhibited by the crystal obtained in Comparative Example 1.

m.p. 161°–163° C.

| Elemental analysis for $C_{32}H_{30}N_2O_3$ | C | H | N |
|---|---|---|---|
| Cal'd: | 78.34% | 6.16% | 5.71% |
| Found: | 78.38% | 6.13% | 5.75% |

EXAMPLE 3

Production of the β-Type Crystal Modification of 2-(3-methylanilino)-3-methyl-6-diethylamino-fluoran Ten grams of the α-type crystal modification of 2-(3-methylanilino)-3-methyl-6-diethylaminofluoran was dissolved by refluxing in 150 ml of a toluene/methanol (¼) solvent system for 1 h and cooled. The resulting precipitate was recovered by filtration and dried to produce a pale yellowish white crystal in an amount of 8.3 g. The melting point and elemental analysis of the crystal were as listed below. An X-ray diffraction diagram for the crystal, as well as its parent peak of mass analysis and IR absorption spectrum were the same as those of the crystal obtained in Example 1.

m.p. 189°–190° C.

| Elemental analysis for $C_{32}H_{30}N_2O_3$ | C | H | N |
|---|---|---|---|
| Cal'd: | 78.34% | 6.16% | 5.71% |
| Found: | 78.36% | 6.17% | 5.70% |

The same procedure was repeated except the toluene/methanol solvent system used for recrystallization was replaced by a toluene/ethanol solvent system, a toluene/isopropanol solvent system, a toluene/n-butanol solvent system, a benzene/methanol solvent system and a mixed xylene/methanol solvent system, but the results were the same.

EXAMPLE 4

Production of Pressure-Sensitive Recording Material

Three grams of the β-type crystal modification of 2-(3-methylanilino)-3-methyl-6-diethylaminofluoran as produced in Example 1 was dissolved in 47 g of KMC-113 (solvent available from Kureha Chemical Industry Co., Ltd.) under heating, thereby preparing a solution of the color former.

In a separate step, 5 g of an aqueous solution of 20% (specialty) anionic copolymer (available From Mitsui Toatsu Chemicals Inc. under the trade name "SM-100") was added to 100 g of water and the mixture was adjusted to pH 4 by adding an aqueous solution of sodium hydroxide. To the thus adjusted mixture, the solution of the color former 50 g) and a melamine-formaldehyde prepolymer (10 g) (available from Mitsui Toatsu Chemicals Inc. under the trade name "UMC-300") were added and the mixture was emulsified with a homomixer until the size of oil droplets was reduced to 4 microns. Subsequently, the emulsion was heated to 60° C. under agitation, which was continued for an additional one hour at the same temperature. After cooling to room temperature, the emulsion was adjusted to pH 7.5 with 25% aqueous ammonia for preparing a dispersion of encapsulated color former.

Ten grams of the thus prepared dispersion of encapsulated color former, 2 g of wheat starch and 1 g of a latex were mixed well and coated onto a sheet of woodfree paper to give a solids deposit of 5 g/m². The coating was dried to prepare white upper leaf.

EXAMPLE 5

Production of Thermal Recording Material

The β-type crystal modification (5 g) of 2-(3-methylanilino)-3-methyl-6-diethylaminofluoran as produced in Example 1 was pulverized to an average particle size of 1 micron in an aqueous solution (45 g) of 2.5% poly(vinyl alcohol) by means of a sand mill, whereby a dispersion of the color former was prepared.

In a separate step, 10 g of bisphenol A as a color developer and 10 g of p-benzylbiphenyl as a sensitizer were pulverized to an average particle size of 3 microns in an aqueous solution (80 g) of 2.5% poly(vinyl alcohol) by means of a sand mill, whereby a dispersion of the color developer was prepared.

The two dispersions were mixed together; to the mixture, a 50% dispersion of calcium carbonate (30 g) and a 30% dispersion of paraffin wax (15 g) were added and mixed well to form a heat-sensitive coating dispersion.

The thus prepared coating dispersion was applied to a sheet of wood-free paper to give a solids deposit of 4.5 g/m². After drying, the thermal recording layer was adjusted to a Bekk smoothness of 400–500 sec by calendering. In this way, a thermal recording material was prepared.

EXAMPLE 6

Production of Thermal Recording Material

A thermal recording material was prepared by repeating the procedure of Example 5 except that the p-benzylbiphenyl used as sensitizer was replaced by m-terphenyl.

EXAMPLE 7

Production of Thermal Recording Material

A thermal recording material was prepared by repeating the procedure of Example 5 except that the p-benzylbiphenyl used as sensitizer was replaced by 2-benzyloxynaphthalene.

EXAMPLE 8

Production of Thermal Recording Material

A thermal recording material was prepared by repeating the procedure of Example 5 except that the p-benzylbiphenyl used as sensitizer was replaced by di-(p-methylbenzyl) oxalate.

EXAMPLE 9

Production of Thermal Recording Material

A thermal recording material was prepared by repeating the procedure of Example 5 except that the p-benzylbiphenyl used as sensitizer was replaced by 1,2-di-m-toluoxyethane.

Comparative Example 4

Production of Pressure-Sensitive Recording Material

An upper leaf was prepared by repeating the procedure of Example 4 except that the β-type crystal modification of 2-(3-methylanilino)-3-methyl-6-diethylaminofluoran used as color former was replaced by the α-type crystal modification of 2-(3-methylanilino)-3-methyl-6-diethylaminofluoran prepared in Comparative Example 1.

Comparative Example 5

Production of Pressure-Sensitive Recording Material

An upper leaf was prepared by repeating the procedure of Example 4 except that the β-type crystal modification of 2-(3-methylanilino)-3-methyl-6-diethylaminofluoran used as color former was replaced by 2-(2-methylanilino)-3-methyl-6-diethylaminofluoran [compound of formula (2)].

Comparative Example 6

Production of Pressure-Sensitive Recording Material

An upper leaf was prepared by repeating the procedure of Example 4 except that the β-type crystal modification of 2-(3-methylanilino)-3-methyl-6-diethylaminofluoran used as color former was replaced by 2-(4-methylanilino)-3-methyl-6-diethylaminofluoran [compound of formula (3)].

Comparative Example 7

Production of Thermal Recording Material

A thermal recording material was prepared by repeating the procedure of Example 5 except that the β-type crystal modification of 2-(3-methylanilino)-3-methyl-6-diethylaminofluoran used as color former was replaced by the α-type crystal modification of 2-(3- methylanilino)-3-methyl-6-diethylaminofluoran as produced in Comparative Example 1.

Comparative Example 8

Production of Thermal Recording Material

A thermal recording material was prepared by repeating the procedure of Example 5 except that the β-type crystal modification of 2-(3-methylanilino)-3-methyl-6-diethylaminofluoran used as color former was replaced by 2-(2-methylanilino)-3-methyl-6-diethylaminofluoran [compound of formula (2)].

Comparative Example 9

Production of Thermal Recording Material

A thermal recording material was prepared by repeating the procedure of Example 5 except that the β-type crystal modification of 2-(3-methylanilino)-3-methyl-6-diethylaminofluoran used as color former was replaced by 2-(4-methylanilino)-3-methyl-6-diethylaminofluoran [compound of formula (3)].

Evaluation 1

Solubility Test

The β-type crystal modification of 2-(3-methylanilino)-3-methyl-6-diethylaminofluoran prepared in Example 1 was measured for its solubility in two solvents for pressure-sensitive recording materials, i.e., KMC-113 (dialkylnaphthalene derivatives of Kureha Chemical Industry Co., Ltd.) and SAS-29 (diphenylethane derivatives of Nippon Oil Co., Ltd.) Solubility in those solvents was also measured on the following comparative materials: 2-(2-methyl-anilino)-3-methyl-6-diethylaminofluoran [compound of formula (2)] and 2-(4-methylanilino)-3-methyl-6-diethylaminofluoran [compound of formula (3)].

Solubility measurements were performed by the following method. A liquid mixture of about 10 w/w % fluoran compound with solvent was heated on a hot plate at 110°±2.5° C. to form a solution. The solution was transferred into a conical flask equipped with a ground stopper and the contents were stirred at 20°±0.1° C. for 48 h. After filtering off the precipitating fluoran compound, about 1 g of the filtrate was weighed accurately and put into a 100-ml measuring flask; thereafter, 95% acetic acid was added to make a total of 100 ml. A 2-ml portion of the resulting solution was put into a 100-ml measuring flask and 95% acetic acid was added to make a total of 100 ml. The absorbance of the colored solution at a wavelength of maximum absorption in the visible region was measured on a spectrophotometer using 95% acetic acid as a control. The amount of the dissolved fluoran compound was determined from a preliminarily constructed calibration curve and the percentage of dissolved amount was calculated. This procedure was repeated for all test samples and the results are shown in Table 1 below.

TABLE 1

| Sample | Dissolved amount (%) | |
|---|---|---|
| | KMC-113 | SAS-296 |
| compound of Example 1 | 3.4 | 3.1 |
| compound of formula (2) (comparison) | 0.2 | 0.3 |
| compound of formula (3) (comparison) | 0.8 | 0.9 |

Evaluation 2

Testing the Quality and Performance of Pressure-Sensitive Recording Materials

The CB surface of each of the upper leaves prepared in Example 4 and Comparative Examples 4–6 was measured for whiteness and tested for lightfastness (the CB surface was the side of the upper leaf onto which the pressure-sensitive coating dispersion was applied). The test and the measurement were conducted by the following methods.

Whiteness:
  The color density of the CB surface was measured as optical density on a reflection densitometer RD-914 (Macbeth Instrument Corporation).

Lightfastness:
  The CB surface was illuminated with a fluorescent lamp ($2 \times 10^4$ lux) for 72 h and the color density of that surface was measured similarly.

Subsequently, another the group of the upper leaves prepared in Example 4 and a Comparative Examples 4–6 were superposed on lower leaves (having a zinc salt of salicylic acid derivative coated as a color developer) in such a way that the coated surfaces of both leaves would contact each other. Thereafter, the assembly was passed between minirollers at a pressure of 100 kgf/cm² to develop a color. The color developed in each sample was checked subjectively. At the same time, the density of each color image (in OD values) was measured on a reflection densitometer RD-914.

In the next place, the lightfastness of the image formed on each sample of the recording materials was tested by the following method.

Lightfastness measurement:
  Each color image was illuminated with a fluorescent lamp ($2 \times 10^4$ lux) for 72 h and the image density (in OD values) was measured with a reflection densitometer RD-914.

The results of measurements and tests are shown in Table 2.

TABLE 2

| | Performance of the CB surface | | | Image performance | |
|---|---|---|---|---|---|
| | | | | initial color | |
| Run No. | whiteness (OD) | lightfastness (OD) | Image color | image density (OD) | lightfastness (OD) |
| Ex. 4 | 0.08 | 0.23 | black | 0.51 | 0.51 |
| Comp. Ex. 4 | 0.10 | 0.26 | black | 0.48 | 0.46 |
| Comp. Ex. 5 | 0.11 | 0.29 | purplish black | 0.51 | 0.44 |
| Comp. Ex. 6 | 0.11 | 0.25 | greenish black | 0.47 | 0.43 |

Whiteness of the CB surface:
  The smaller the value, the higher the whiteness.

Lightfastness of the CB surface:
  The smaller the value, the higher the lightfastness of the CB surface.

Initial color image density:
  The greater the value, the higher the initial color density.

Lightfastness of the image:
  The greater the value, the higher the lightfastness of the image.

Evaluation 3

Testing the Quality and Performance of Thermal Recording Materials

The whiteness and storage stability of the background of each of the thermal recording materials prepared in Examples 5-9, and Comparative Examples 7-9 were tested, and their dynamic sensitivity for color formation was measured by the following methods.

Whiteness of the background:
The background color density of each sample was measured as optical density on a reflection densitometer RD-914 (Macbeth Instrument Corporation)

Heat resistance of the background:
Each sample was exposed to 60° C.×20% RH for 72 h and the background color density (in OD values) was measured on a reflection densitometer RD-914.

Lightfastness of the background:
Each sample was illuminated with a fluorescent lamp (2×10⁴ lux) for 72 h and the background color density (in OD values) was measured on a reflection densitometer RD-914.

Dynamic sensitivity for color formation:
In recording with a printer TH-PMD (Ohkura Electric Co., Ltd.), the width of pulses that produced an initial color image density of 1.0 based on OD values was measured and the value of applied energy was calculated by the following equation.

Conditions of measurement
Applied voltage: 24 V
Resistance at head: 1640Ω
Pulse period: 2 ms
Applied pulse width: 0.15-1.95 ms Applied energy (mJ/dot) = Power (W/dot × applied pulse width The results of all tests and measurements are shown in Table 3 below.

TABLE 3

| Run No. | back-ground white-ness (OD) | Background storage stability heat resistance (OD) | light-fastness (OD) | Dynamic Sensitivity for color formation (mJ/dot) |
|---|---|---|---|---|
| Ex. 5 | 0.09 | 0.16 | 0.20 | 0.256 |
| 6 | 0.10 | 0.16 | 0.20 | 0.250 |
| 7 | 0.09 | 0.14 | 0.19 | 0.259 |
| 8 | 0.09 | 0.14 | 0.19 | 0.249 |
| 9 | 0.10 | 0.15 | 0.18 | 0.248 |
| Comp. Ex. 7 | 0.14 | 0.17 | 0.30 | 0.254 |
| 8 | 0.11 | 0.12 | 0.45 | 0.279 |
| 9 | 0.14 | 0.17 | 0.32 | 0.272 |

Background whiteness:
The smaller the value, the higher the whiteness of the background.

Background storage stability:
The smaller the value after each test, the higher the storage stability of the background.

Dynamic sensitivity for color formation:
The smaller the value, the higher the sensitivity for color formation.

Subsequently, another group of the thermal recording materials prepared in Examples 5-9 and Comparative Examples 7-9 were permitted to develop color with the printer TH-PMD at a pulse width of 0.95 ms, and the image density (in OD values) on each sample was measured with the Macbeth RD-914.

In the next place, the images obtained were tested for their storage stability in accordance with the following methods:

Image resistance to hot humidity:
Each color image was exposed to 50° C.×90% RH for 72 h and, thereafter, the image density (in OD values) was measured on a reflection densitometer RD-914.

Image resistance to heat:
Each color image was exposed to 60° C.×20% RH for 72 h and, thereafter, the image density (in OD values) was measured on a reflection densitometer RD-914.

Image lightfastness:
Each color image was illuminated with a fluorescent lamp (2×10⁴ lux) for 72 h and, thereafter, the image density (in OD values) was measured on a reflection densitometer RD-914.

The color fastness of each image was expressed by the following formula:

$$\text{Color fastness (\%)} = \frac{\text{Image density after test}}{\text{Initial color image density}} \times 100$$

The results of all measurements and tests are shown in Table 4 below.

TABLE 4

| Run No. | Image color | Initial color image density (OD value) | Color fastness of image hot humidity resistance (%) | heat resistance (%) | light-fastness (%) |
|---|---|---|---|---|---|
| Ex. 5 | black | 1.11 | 81 | 80 | 90 |
| 6 | black | 1.11 | 79 | 84 | 91 |
| 7 | black | 1.12 | 83 | 82 | 87 |
| 8 | black | 1.15 | 78 | 76 | 84 |
| 9 | black | 1.16 | 87 | 80 | 87 |
| Comp. Ex. 7 | black | 1.09 | 72 | 72 | 83 |
| 8 | purplish black | 1.09 | 70 | 72 | 81 |
| 9 | greenish black | 1.10 | 75 | 73 | 82 |

Initial color image density:
The greater the value, the higher the initial color density.

Color fastness of image:
The greater the value, the greater the color fastness of image.

As one can see from Table 1, the β-type crystal modification of 2-(3-methylanilino)-3-methyl-6-diethylaminofluoran of the present invention has high solubility in inner-phase solvents compared to compounds having similar structures. As is also clear from Tables 2-4, pressure-sensitive and thermal recording materials that use as a color former the β-type crystal modification of 2-(3-methylanilino)-3-methyl-6-diethylaminofluoran according to the present invention have the advantage that the CB surface and the background have a higher degree of whiteness and storage stability as accompanied by better color rendition than recording materials that use the α-type crystal modification of the same structure and compounds of similar structures. In addition, the recording materials using the color former of the present invention have higher sensitivity for color formation and greater color fastness of image.

Thus, the β-type crystal modification of 2-(3-methylanilino)-3-methyl-6-diethylaminofluoran under consideration is very useful as a color former for various recording materials including a pressure-sensitive recording material and a thermal recording material.

What is claimed is:

1. In a recording material that utilizes the color reaction between an electron donating color former and an electron accepting color developer, the improvement wherein there is contained as the electron donating color former a β-type crystal modification of 2-(3-methylanilino)-3-methyl-6-diethylaminofluoran that is characterized by characteristic peaks at diffraction angles at $2\theta° \pm 0.2°$ of 7.6°, 12.2°, 14.9°, 15.9°, 17.6° and 22.8° on X-ray diffractiometry using Cu-Kα rays and which has a melting point in the range of 186°–191° C.

2. A recording material according to claim 1 which is a pressure-sensitive recording material.

3. A recording material according to claim 1 which is a thermal recording material.

4. A thermal recording material according to claim 3 which uses bisphenol A as the electron accepting color developer and which uses at least one sensitizer selected from among p-benzylbiphenyl, m-terphenyl, 2-benzyloxynaphthalene, di-(p-methylbenzyl) oxalate and 1,2-di-m-toluoxyethane.

* * * * *